US009782205B2

(12) United States Patent
Marrero, Sr.

(10) Patent No.: US 9,782,205 B2
(45) Date of Patent: Oct. 10, 2017

(54) CURVED TIBIOTALAR FUSION NAIL AND METHOD OF USE

(71) Applicant: CMARR ENTERPRISES, LLC, New Orleans, LA (US)

(72) Inventor: Roy R. Marrero, Sr., New Orleans, LA (US)

(73) Assignee: CMARR ENTERPRISES, LLC, New Orleans, LA (US)

( * ) Notice: Subject to any disclaimer, the term of this patent is extended or adjusted under 35 U.S.C. 154(b) by 0 days.

(21) Appl. No.: 14/898,310

(22) PCT Filed: Jul. 2, 2014

(86) PCT No.: PCT/US2014/045259
§ 371 (c)(1),
(2) Date: Dec. 14, 2015

(87) PCT Pub. No.: WO2015/017074
PCT Pub. Date: Feb. 5, 2015

(65) Prior Publication Data
US 2016/0135857 A1 May 19, 2016

Related U.S. Application Data

(60) Provisional application No. 61/957,443, filed on Jul. 2, 2013.

(51) Int. Cl.
*A61B 17/56* (2006.01)
*A61B 17/58* (2006.01)
(Continued)

(52) U.S. Cl.
CPC .......... *A61B 17/72* (2013.01); *A61B 17/1725* (2013.01)

(58) Field of Classification Search
CPC ........................................ A61B 17/72–17/7291
(Continued)

(56) References Cited

U.S. PATENT DOCUMENTS 3,977,398 A * 8/1976 Burstein ............ A61B 17/7283
606/62
4,135,507 A * 1/1979 Harris ................ A61B 17/7208
606/62
(Continued)

FOREIGN PATENT DOCUMENTS

WO WO-2011/072249 A1 6/2011

OTHER PUBLICATIONS

Bluman et al., Tibiotalar arthrodesis, Sem. Arthroplasty, 21(4):240-6 (2010).
(Continued)

*Primary Examiner* — Eduardo C Robert
*Assistant Examiner* — Michelle C Eckman
(74) *Attorney, Agent, or Firm* — Marshall, Gerstein & Borun LLP

(57) ABSTRACT

A tibiotalar fusion system includes that includes a curved fusion nail and interlocking fasteners, along with delivery instrumentation. The curved ankle fusion nail is delivered with the fasteners in such a manner that the curved ankle fusion nail does not pass through the subtalar (talocalcaneal) joint. The curved fusion nail thus preserves the subtalar (talocalcaneal) joint and the natural motion of the hindfoot within a mammal such as, for example, a human. Additionally, drill guided delivery instrumentation and surgical methods of delivering and fixing the curved tibiotalar nail within a desired anatomical location such as the ankle.

19 Claims, 7 Drawing Sheets

(51) Int. Cl.
  *A61F 2/30* (2006.01)
  *A61B 17/72* (2006.01)
  *A61B 17/17* (2006.01)

(58) Field of Classification Search
  USPC .................................................. 606/62–68
  See application file for complete search history.

(56) References Cited

U.S. PATENT DOCUMENTS

| | | | | |
|---|---|---|---|---|
| 5,034,012 | A * | 7/1991 | Frigg | A61B 17/8861 606/104 |
| 5,035,697 | A * | 7/1991 | Frigg | A61B 17/7283 606/329 |
| 5,041,115 | A * | 8/1991 | Frigg | A61B 17/72 606/62 |
| 5,374,235 | A * | 12/1994 | Ahrens | A61B 17/7233 606/101 |
| 6,010,505 | A * | 1/2000 | Asche | A61B 17/683 606/62 |
| 6,010,506 | A * | 1/2000 | Gosney | A61B 17/72 606/62 |
| 6,210,414 | B1 * | 4/2001 | Lin | A61B 17/72 606/62 |
| 6,322,591 | B1 * | 11/2001 | Ahrens | A61B 17/72 606/62 |
| 6,355,041 | B1 * | 3/2002 | Martin | A61D 1/00 606/281 |
| 6,454,810 | B1 * | 9/2002 | Lob | A61B 17/72 606/62 |
| 6,527,775 | B1 * | 3/2003 | Warburton | A61B 17/164 606/62 |
| 6,629,976 | B1 * | 10/2003 | Gnos | A61B 17/7291 606/62 |
| 2002/0099379 | A1 * | 7/2002 | Adam | A61B 17/72 606/67 |
| 2002/0103488 | A1 * | 8/2002 | Lower | A61B 17/72 606/62 |
| 2002/0107578 | A1 * | 8/2002 | Speitling | A61B 17/7233 623/23.6 |
| 2003/0073999 | A1 * | 4/2003 | Putnam | A61B 17/1782 606/62 |
| 2003/0097131 | A1 | 5/2003 | Schon et al. | |
| 2005/0107791 | A1 | 5/2005 | Manderson | |
| 2006/0015101 | A1 * | 1/2006 | Warburton | A61B 17/1668 606/62 |
| 2006/0015123 | A1 * | 1/2006 | Fencl | A61B 17/1659 606/104 |
| 2006/0161155 | A1 * | 7/2006 | Schlienger | A61B 17/72 606/62 |
| 2006/0200141 | A1 * | 9/2006 | Janna | A61B 17/72 606/62 |
| 2006/0200142 | A1 * | 9/2006 | Sohngen | A61B 17/72 606/62 |
| 2007/0123878 | A1 * | 5/2007 | Shaver | A61B 17/72 606/64 |
| 2007/0173835 | A1 * | 7/2007 | Medoff | A61B 17/72 606/62 |
| 2007/0276385 | A1 * | 11/2007 | Schlienger | A61B 17/72 606/71 |
| 2007/0288017 | A1 * | 12/2007 | Kaup | A61B 17/72 606/62 |
| 2007/0288097 | A1 * | 12/2007 | Hurowitz | A61B 17/72 623/47 |
| 2008/0009869 | A1 * | 1/2008 | Schlienger | A61B 17/72 606/64 |
| 2008/0132896 | A1 * | 6/2008 | Bowen | A61B 17/1604 606/80 |
| 2008/0221574 | A1 * | 9/2008 | Cavallazzi | A61B 17/1739 606/62 |
| 2008/0221577 | A1 | 9/2008 | Elghazaly | |
| 2009/0157077 | A1 * | 6/2009 | Larsen | A61B 17/1725 606/62 |
| 2010/0137865 | A1 * | 6/2010 | Frankle | A61B 17/1725 606/64 |
| 2010/0292722 | A1 * | 11/2010 | Klaue | A61B 17/1642 606/167 |
| 2010/0305623 | A1 | 12/2010 | Klaue | |
| 2011/0160728 | A1 * | 6/2011 | Blitz | A61B 17/1725 606/64 |
| 2011/0166608 | A1 | 7/2011 | Duggal et al. | |
| 2011/0172667 | A1 * | 7/2011 | Richards | A61B 17/72 606/62 |
| 2011/0295252 | A1 * | 12/2011 | Tipirneni | A61B 17/685 606/62 |
| 2012/0010719 | A1 * | 1/2012 | Reiley | A61B 17/72 623/21.18 |
| 2012/0209268 | A1 * | 8/2012 | Overes | A61B 17/1725 606/62 |
| 2012/0245642 | A1 * | 9/2012 | Giannoudis | A61B 17/1725 606/280 |
| 2012/0330313 | A1 * | 12/2012 | Grady | A61B 17/7225 606/64 |
| 2013/0072931 | A1 * | 3/2013 | Homeier | A61B 17/56 606/62 |
| 2013/0158553 | A1 * | 6/2013 | Nardini | A61B 17/863 606/64 |
| 2013/0325006 | A1 * | 12/2013 | Michelinie | A61B 17/7291 606/62 |
| 2014/0031881 | A1 | 1/2014 | Bales | |
| 2014/0066932 | A1 * | 3/2014 | Appenzeller | A61B 17/1725 606/64 |
| 2014/0114312 | A1 * | 4/2014 | Krause | A61B 17/8625 606/62 |
| 2014/0142575 | A1 * | 5/2014 | Biedermann | A61B 17/846 606/62 |
| 2014/0309636 | A1 * | 10/2014 | Meek | A61B 17/7208 606/62 |
| 2015/0073414 | A1 * | 3/2015 | Rogachefsky | A61B 17/7291 606/64 |
| 2015/0112343 | A1 * | 4/2015 | Medoff | A61B 17/1725 606/64 |
| 2015/0150608 | A1 * | 6/2015 | Sammarco | A61B 17/1725 606/64 |
| 2015/0230837 | A1 * | 8/2015 | Kaup | A61B 17/7241 606/64 |
| 2016/0338842 | A1 * | 11/2016 | Adams | A61B 17/68 |

OTHER PUBLICATIONS

International Search Report and Written Opinion, International Application No. PCT/US14/45259, dated Jan. 2, 2015.
Extended European Search Report, European patent application No. 14832221.7, dated Feb. 17, 2017.

* cited by examiner

CURVED TIBIOTALAR FUSION NAIL AND METHOD OF USE

REFERENCE TO RELATED APPLICATION

This application claims the benefit of the filing date of U.S. Provisional Application No. 61/957,433, filed on Jul. 2, 2013. U.S. Provisional Application No. 61/957,433 is hereby incorporated by reference.

FIELD OF DISCLOSURE

The present application generally relates bone fusion systems and methods, and more particularly, to bone fusion nails for repairing or treating an injury to an ankle joint area or a degenerative joint disease affecting an ankle joint area, instruments for delivering bone fusion nails and surgical methods of using bone fusion nails.

BACKGROUND

Painful degenerative joint disease of the ankle can be caused by many conditions including osteoarthritis, rheumatoid arthritis, trauma and deformity. These conditions are typically treated by surgical methods including fusion with screw fixation, fusion with intramedullary nailing, or a total ankle arthroplasty. Each of these choices presents significant problems. For instance, a screw used in fusion screw fixation may loosen over time and result in loss of fixation. Fusion screw fixation also involves a risk of screw migration or breakage, and may necessitate prolonged post-operative non-weight-bearing limitations on the patient. Traditional intramedullary nailing options may provide a stronger construct than fusion screw fixation and permit earlier post-operative weight-bearing activities by the patient. However, traditional intramedullary nails span the subtalar (talocalcaneal) joint and thus destroy the subtalar (talocalcaneal) joint. This aspect of traditional intramedullary nails severely limits motion of the hindfoot and makes it difficult to walk, especially on uneven surfaces. Another problem with traditional intramedullary nails is that such nails transfer a significant amount of stress to other joints of the foot, which can lead to degeneration of these joints, additional pain, and in some cases, require further surgical intervention. Because total ankle arthroplasty typically has an unacceptably high failure rate, ankle fusion is generally viewed as a more reliable choice for the treatment of degenerative joint disease of the ankle.

Currently available intramedullary nailing options, while better than most other treatment options, each require the fusion nail to be inserted through the heel bone or calcaneus bone, through the subtalar (talocalcaneal) joint, up through the talus bone, through the tibiotalar joint, and into the tibia. A need therefore exists for devices and methods for delivering a secured fusion nail that bypasses and preserves the subtalar (talocalcaneal) joint.

SUMMARY

A tibiotalar fusion system is disclosed that allows for the bypass of the subtalar (talocalcaneal) joint and includes a curved fusion nail and interlocking fasteners along with delivery and targeting instrumentation. The fasteners are used to secure the placement of the curved fusion nail in a desired anatomical location. The curved fusion nail is dimensioned so that it does not pass through the subtalar (talocalcaneal) joint, and thus preserves the subtalar joint and the natural motion of the hindfoot within a mammal, such as, a human.

Also disclosed are delivery instruments such as drill guide jigs that facilitate placement of the curved fusion nail within a desired location, such as an ankle joint area, and allow for precise specific fastener placement within the curved fusion nail.

Further disclosed are surgical methods of using the curved fusion nail for repair of ankle trauma, deformity, and/or treatment of degenerative ankle joints.

BRIEF DESCRIPTION OF SEVERAL VIEWS OF THE DRAWINGS

Embodiments and/or variations are now described by way of example with reference to the accompanying drawings.

DETAILED DESCRIPTION

Described herein is a curved tibiotalar fusion system including a curved fusion nail and interlocking fasteners along with delivery and targeting instrumentation, and additionally, surgical methods for using a tibiotalar fusion system. The presently disclosed curved tibiotalar fusion system and surgical methods may be utilized for the fusion of degenerative joints, such as, for example, a tibiotalar joint fusion. Also disclosed are delivery and targeting instrumentations, such as, for example, a drill guide jig, to currently align the fasteners with the curved fusion nail after the curved fusion nail is placed in the desired bone tissue surrounding the targeted joint, such as, for example, a tibiotalar joint.

Figure 1:
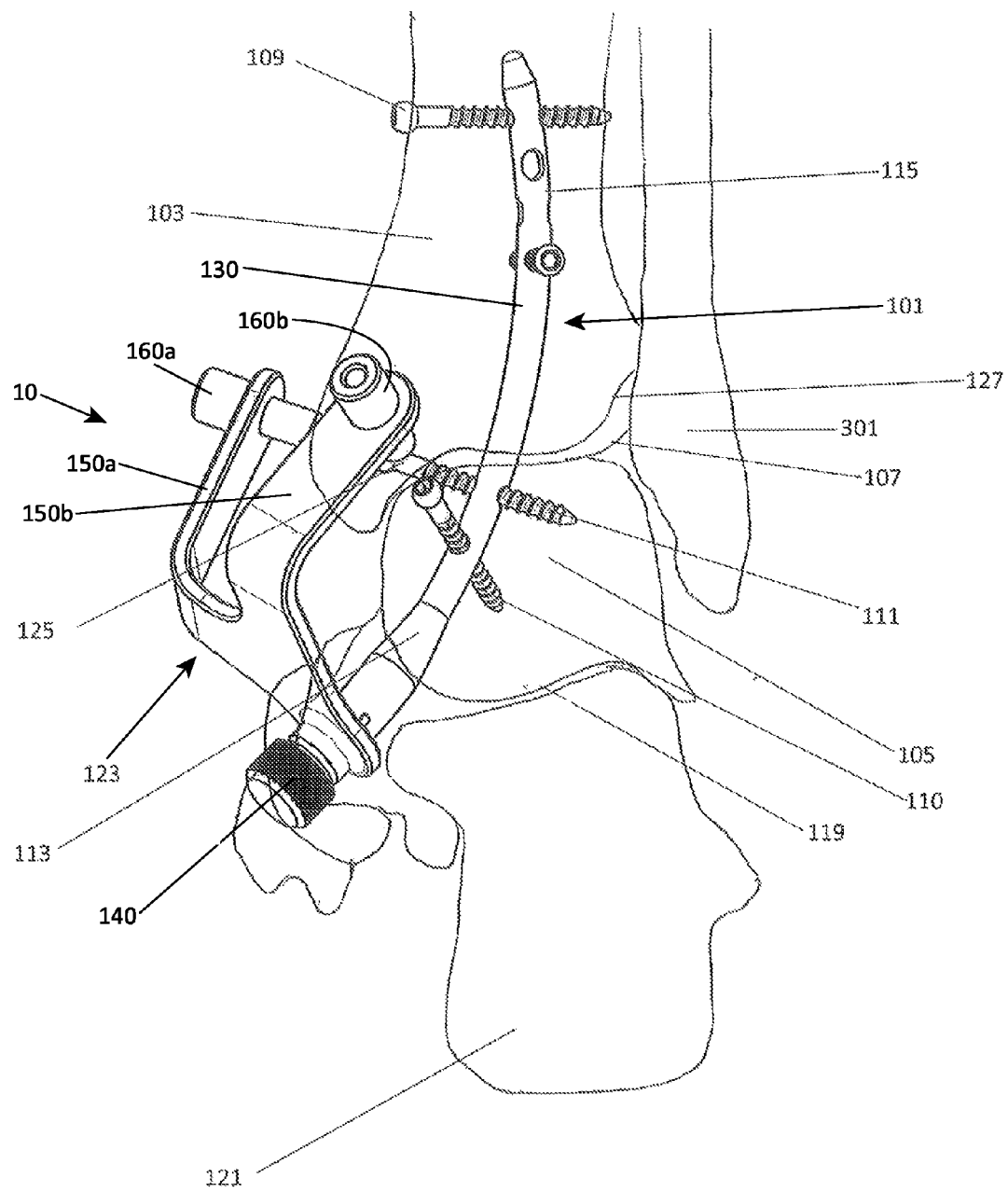
FIG. 1 illustrates a back view of an embodiment of a tibiotalar fusion system, including a curved fusion nail and delivery instrumentation, positioned within and around a human lower leg and foot, in accordance with principles of the present disclosure.
Figure 3:
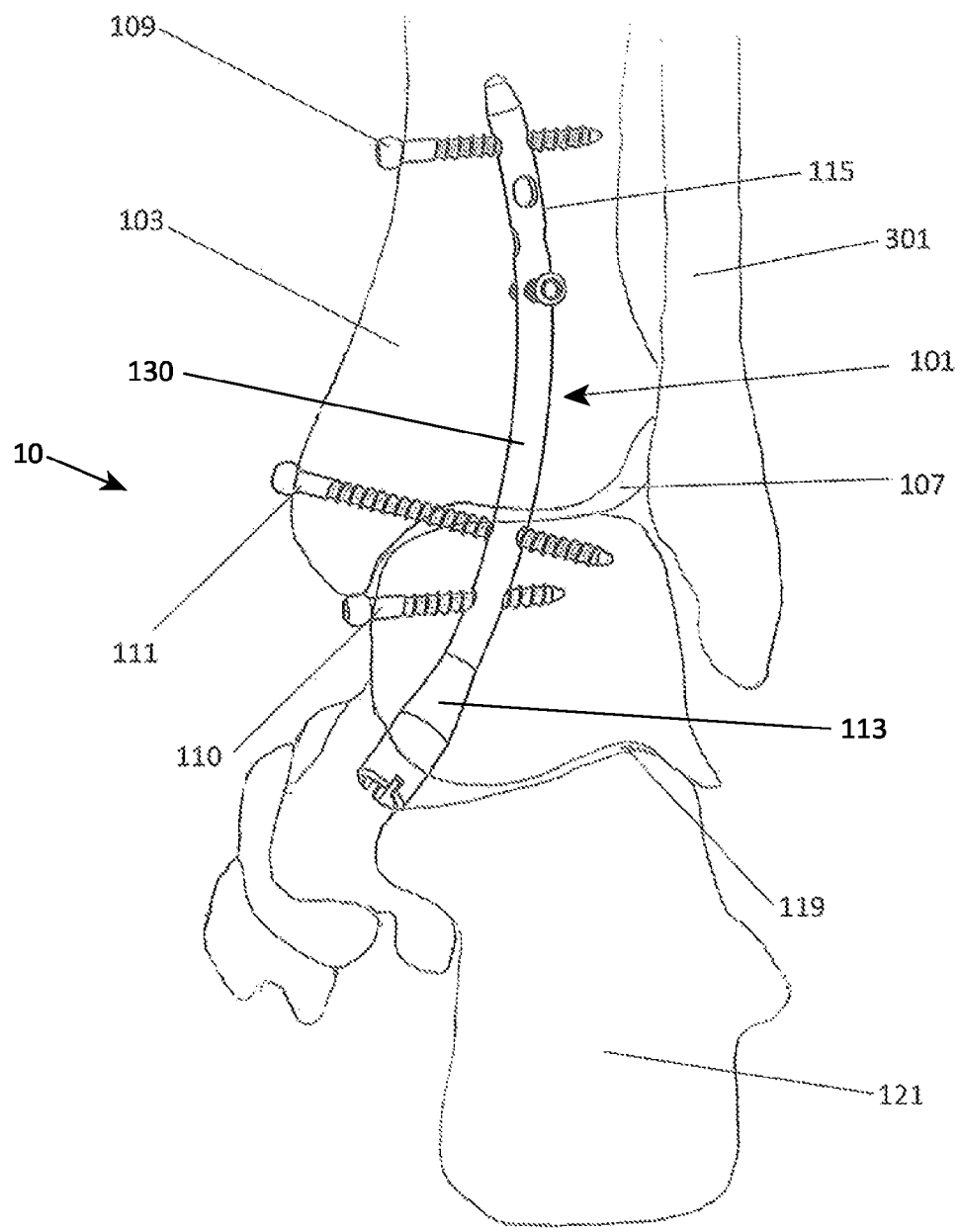
FIG. 3 illustrates a back view an embodiment of a tibiotalar fusion system with the delivery instrumentation removed, in accordance with principles of the present disclosure.

FIG. 1 illustrates a preferred embodiment of a curved tibiotalar fusion system 10 including a rod, such as curved fusion nail 101, placed distally within a tibia 103 and proximally within the talus bone 105 below the ankle (tibiotalar) joint 107. Two fasteners 109 are located distally through the curved fusion nail 101 and the tibia bone 103, and two fasteners 110 and 111 are located in the proximal end of the curved fusion nail 101 within the talus bone 105. As shown in FIG. 3, in the preferred embodiment, one of the proximal fasteners 111 passes through the tibia bone 103, across the ankle (tibiotalar) joint 107, and into the talus bone 105 where it passes through and secures the curved fusion nail 101. In an alternative embodiment, one of the proximal fasteners 110 may be inserted through the talus bone 105, and secured into the fibula 301 for added construct strength.

The curved fusion nail 101 includes a proximal end 113, a distal end 115 and an elongate body 130 extending between the proximal end 113 and the distal end 115. The elongate body 130 is curved in a manner allowing the curved fusion nail 101 to be inserted through the talus bone 105 and into the tibia bone 103 without penetrating the calcaneal bone 121. In one embodiment, at least a portion of the elongate body 130 possesses a radius of curvature in a range between approximately (e.g., ±10%) 1.5 and 4.0 inches, or lesser or greater. For example, at least a portion of the elongate body 130 may possess a radius of curvature in a range between 2.0 and 3.0 inches. Additionally, the proximal end 113 and the distal end 115 of the nail 101 may be curved, as illustrated in the figures, and their respective radiuses of curvature may fall within the previously described ranges. In one embodiment, only the proximal end 113 is curved. The elongate body 130 is not limited to having a single radius of curvature. Different portions of the elongate body 130 may have different radiuses of curvature. For example, the radius of curvature of the middle portion of the elongate body 130 may be greater than the ends of the elongate body 130 such that the elongate body 130 becomes straighter near its ends. The elongate body 130 may have a circular cross section and have a diameter in a range between approximately (e.g., ±10%) 7.0 and 12.0 mm, for example, between 8.0 and 11.0 mm, and, for example, between 9.0 and 10.0 mm. The curved fusion nail 101 may be made of any suitable material for placement within the body, including, but not limited, titanium and/or stainless steel. The curved fusion nail 101 may also be coated with a therapeutic agent to aid in the healing process such as, for example, a bone-growth promoting agent. Each of the fasteners 109, 110, 111 may have an external thread, as shown in the figures, and have a diameter in a range between approximately (e.g., ±10%) 4.0 and 5.5 mm, for example, between 4.5 and 5.0 mm.

In the preferred embodiment of the method disclosed the surgeon would drill a hole along a curved path through the talus bone 105 and the tibia bone 103, then deliver a curved fusion nail 101 by entering the talus bone 105 at an angle deliver the curved fusion nail 101 through the talus bone 105, across the ankle (tibiotalar) joint 107, and then place the curved fusion nail 101 with its distal end 115 within the tibia bone 103. This delivery method preserves the subtalar (talocalcaneal) joint 119 from fusion and maintains normal motion of the hindfoot. Once the curved fusion nail 101 is placed, a drill guide jig 123 is utilized with the curved fusion nail 101 that allows for the accurate placement 125 of the proximal fasteners 110 and 111. The two distal fasteners 109 are then placed through the tibia bone 103 and the curved fusion nail 101.

Figure 2:
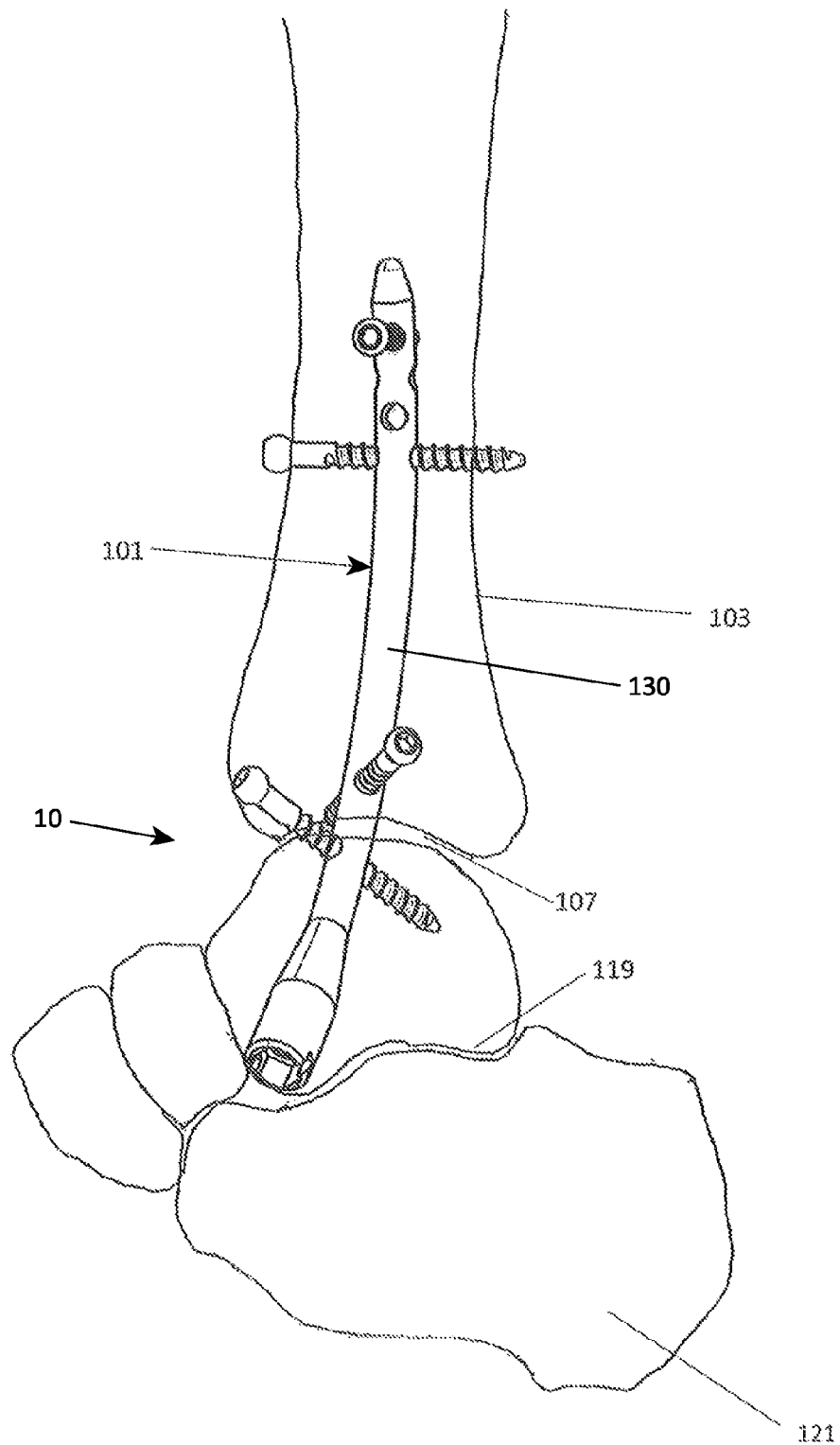
FIG. 2 depicts a side view of an embodiment of a tibiotalar fusion system with the delivery instrumentation removed, in accordance with principles of the present disclosure.

FIG. 2 shows a side view of the delivered curved fusion nail 101, and FIG. 3 shows a back view of the delivered curved fusion nail 101. In one embodiment the lower proximal fastener 110 might be placed through the talus bone 105, and secured into the fibula 301 for added construct strength.

Figure 4:
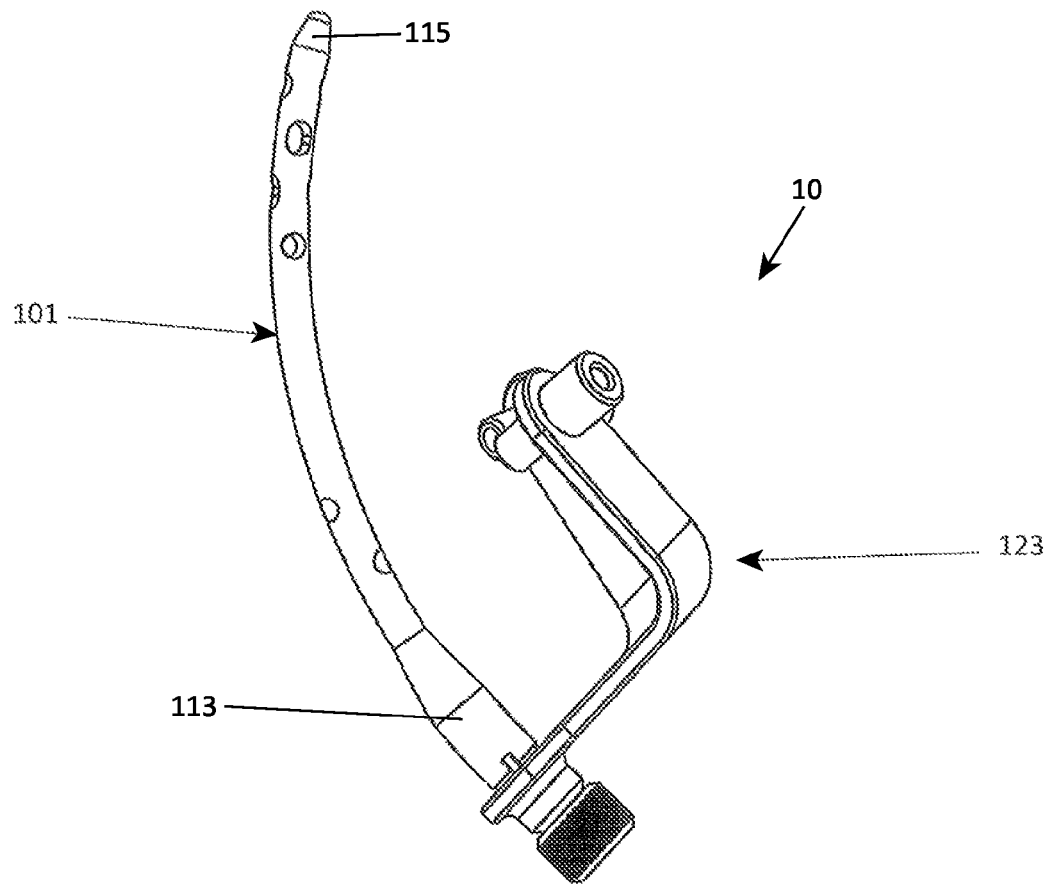
FIG. 4 illustrates an embodiment of a tibiotalar fusion system including a curved fusion nail attached to a delivery drill guide jig instrument, in accordance with principles of the present disclosure.

FIG. 4 illustrates a curved fusion nail 101 with a fastener drill guide jig 123 attached to the proximal end 113 of the curved fusion nail 101. The fastener drill guide jig 123 includes a base 140 that attaches to the proximal end 113 of the curved fusion nail 101, and two stabilization arms 150a, 150b that extend from the base 140. Drill guide sleeves 160a, 160b protrude from the respective free ends of the stabilization arms 150a, 150b and may be pressed against the epidermis (not illustrated) covering the ankle. Each of the drill guide sleeves 160a, 160b includes a central guide passage that permits one of the fasteners 110, 111 to be inserted therethrough, and which aligns the respective fastener with a targeted anatomical region. For example, the guide passage extending through the guide sleeve 160a may guide the fastener 111 along a path that allows the fastener 111 to be inserted through both the tibia bone 103 and the talus bone 105.

Figure 5:
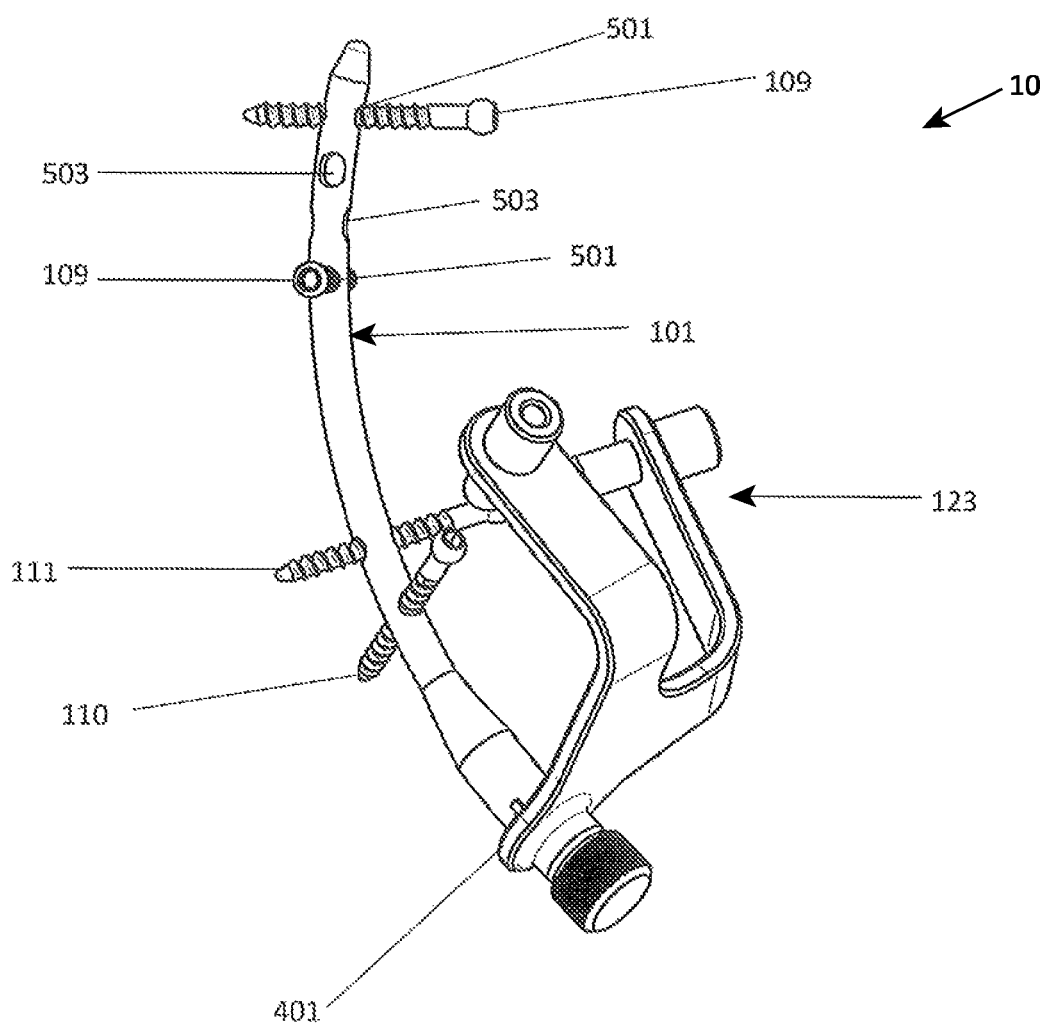
FIG. 5 depicts an embodiment of a tibiotalar fusion system including a curved fusion nail attached to a delivery drill guide jig instrument and fasteners passing through the curved tibiotalar fusion nail, wherein a distal portion of the curved fusion nail contains oval openings that allow for dynamic action of the curved tibiotalar fusion nail after placement in the bone, in accordance with principles of the present disclosure.

In one embodiment, as illustrated in FIG. 5, the hole 503 for the distal fastener 109 may be a non-circular shape such as, for example, an oval shape to allow for the dynamic compression of the fusion apparatus within the tibia bone 103 and the ankle joint by providing for movement of the curved fusion nail 101 over the distal fasteners 109. In another embodiment the curved fusion nail 101, the distal end 115 of curved fusion nail 101 may include two sets of holes 501 and 503, with the holes 501 having, for example, a circular shape for static fastening, and the holes 503 having, for example, an oval shape for dynamic compression fastening, depending on the desire of the user. In one embodiment, the some or all of the holes 501, 503 may have an oval shape for dynamic compression fastening, and the holes for fasteners 110, 111 may each have a circular shape for static fastening.

Figure 6:
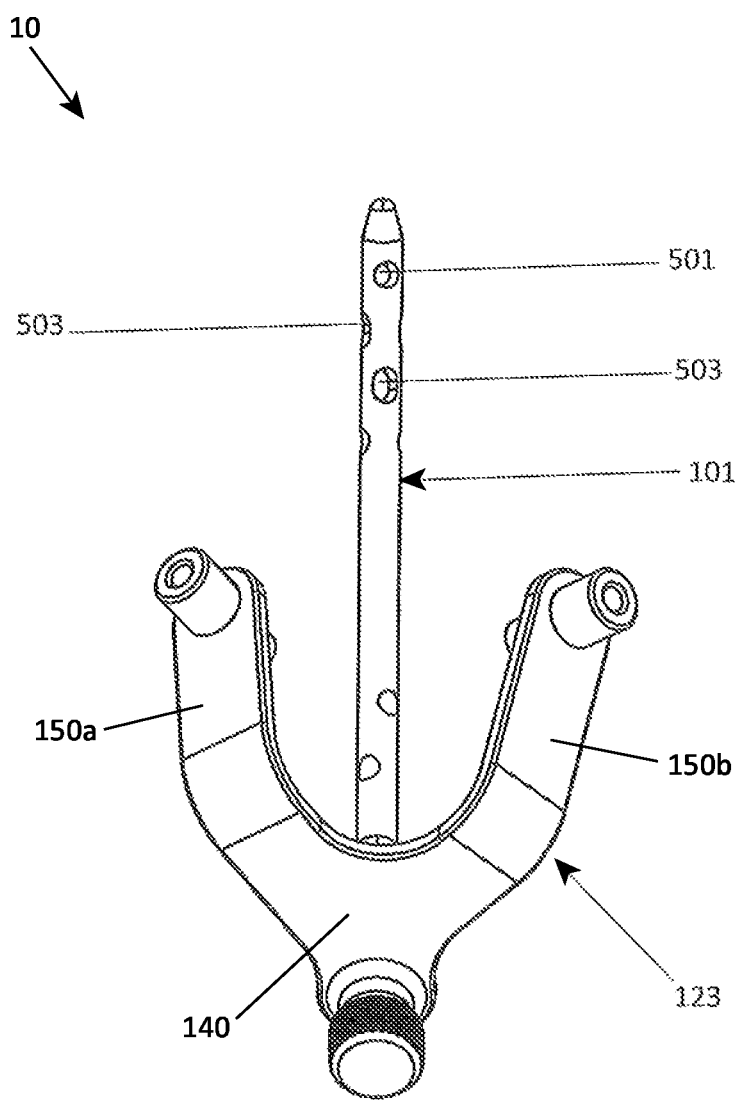
FIG. 6 illustrates a side view of an embodiment of a tibiotalar fusion system including a curved fusion nail attached to a drill guide jig, in accordance with principles of the present disclosure.
Figure 7:
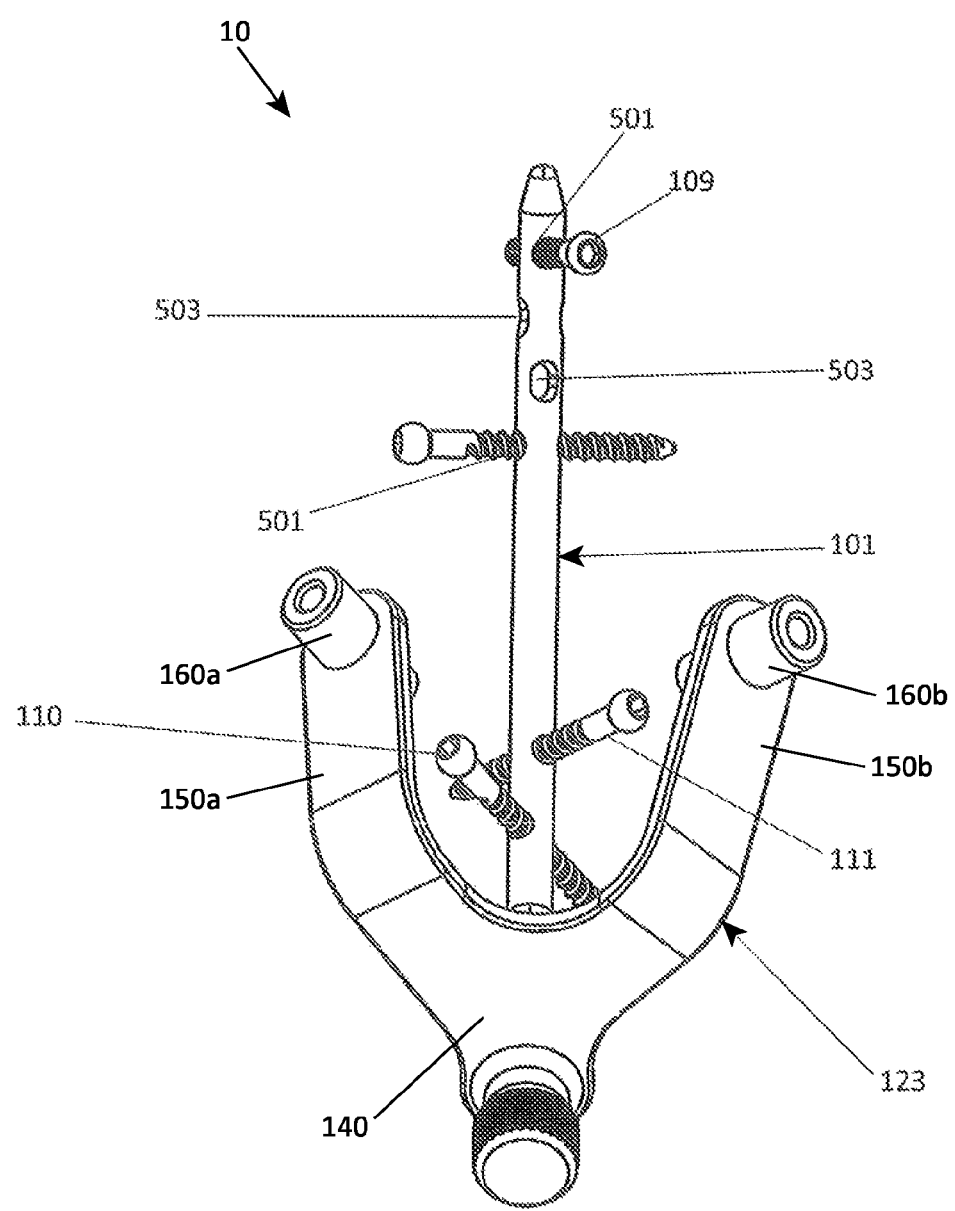
FIG. 7 illustrates a side view of an embodiment of a tibiotalar fusion system including a curved fusion nail with fasteners passing through the various fastener passages and which is attached to a drill guide jig.

FIG. 6 shows a side view of the curved fusion nail 101 attached to a drill guide jig 123. FIG. 7 shows side view of the curved fusion nail 101 with fasteners passing through the various fastener passages.

It will be appreciated by persons skilled in the art that numerous variations and/or modifications may be made to the described device as specifically shown here without departing from the spirit or scope of that broader disclosure. The various examples are, therefore, to be considered in all respects as illustrative and not limiting.

What is claimed is:

1. A tibiotalar fusion system comprising:
    a rod having a proximal end, a distal end, and an elongate body extending between the proximal end and the distal end, the elongate body being curved in a manner allowing the rod to be inserted through a talus bone and a tibial bone without penetrating a calcaneal bone;
    a first hole passing through the elongate body of the rod; and
    a first fastener sized to pass through the first hole in the elongate body of the rod and secure the rod to at least one of the talus bone or the tibial bone;
    wherein at least a portion of the elongate body has a radius of curvature in a range between 1.5 and 4.0 inches.

2. The tibiotalar fusion system of claim 1, the first hole being positioned to allow the first fastener to pass through the tibial bone, across a tibiotalar joint, and into the talus bone.

3. The tibiotalar fusion system of claim 2, a second hole passing through the elongate body of the rod proximate to the distal end of the rod, and a second fastener sized to pass through the second hole and secure the rod to the tibial bone.

4. The tibiotalar fusion system of claim 3, a third hole passing through the elongate body of the rod proximate to the proximal end of the rod, and a third fastener sized to pass through the third hole and secure the rod to the talus bone.

5. The tibiotalar fusion system of claim 4, at least one of the first hole, the second hole, or the third hole being non-circular.

6. The tibiotalar fusion system of claim 4, at least one of the first hole, the second hole, or the third hole being oval-shaped.

7. The tibiotalar fusion system of claim 4, a fourth hole passing through the elongate body of the rod proximate to the distal end of the rod, and a fourth fastener sized to pass through the fourth hole and secure the rod to the tibial bone, the fourth hole and the second hole being crosswise to each other.

8. The tibiotalar fusion system of claim 2, the first fastener having external threads engageable to the tibial bone and the talus bone.

9. The tibiotalar fusion system of claim 1, comprising a drill guide jig having a base and one or more stabilization arms extending from the base, the base being attachable to the proximal end of the rod, each of the one or more stabilization arms including a drill guide sleeve positionable against an epidermis of a patient.

10. The tibiotalar fusion system of claim 1, at least a portion of the elongate body having a radius of curvature in a range between 2.0 and 3.0 inches.

11. A method of fusing together only a talus bone and a tibial bone, the method comprising:
   drilling a hole along a curved path through only the talus bone and the tibial bone;
   inserting a rod through the hole so that the rod spans only the talus bone and the tibial bone, the rod having a proximal end, a distal end, and an elongate body extending between the proximal end and the distal end, the elongate body being curved in a manner corresponding to the curved path of the hole; and
   inserting a first screw through a first hole in the elongate body of the rod and at least one of the talus bone or the tibial bone;
   wherein, at least a portion of the elongate body has a radius of curvature in a range between 1.5 and 4.0 inches.

12. The method of claim 11, and inserting the first screw through the tibial bone and the talus bone so that the first screw spans a tibiotalar joint.

13. The method of claim 12, comprising rotating the first screw in a manner causing external threads of the first screw to pull the talus bone and the tibial bone together and thereby compress the talus bone against the tibial bone.

14. The method of claim 13, comprising inserting a second screw through a second hole in the elongate body of the rod and the tibial bone, and inserting a third screw through a third hole in the elongate body and the talus bone.

15. The method of claim 14, and in inserting the first screw in the first hole, inserting the second screw in the second hole, or inserting the third screw in the third hole, at least one of the first hole, the second hole, or the third hole is non-circular.

16. The method of claim 14, and in inserting the first screw in the first hole, inserting the second screw in the second hole, or inserting the third screw in the third hole, at least one of the first hole, the second hole, or the third hole is oval-shaped.

17. The method of claim 14, comprising inserting a fourth screw, crosswise to the second screw, through a fourth hole in the elongate body of the rod and the tibial bone.

18. The method of claim 11, comprising securing a base of a drill guide jig to the proximal end of the rod prior to inserting the rod into the hole, the drill guide jig having one or more stabilization arms extending from the base, and pressing a drill sleeve which extends from the one or more stabilization arms against an epidermis of a patient.

19. The method of claim 11, at least a portion of the elongate body having a radius of curvature in a range between 2.0 and 3.0 inches.

* * * * *